United States Patent [19]

Pyke

[11] Patent Number: 4,947,104

[45] Date of Patent: Aug. 7, 1990

[54] DEVICE AND METHOD FOR DETECTION OF FLUID CONCENTRATION UTILIZING CHARGE STORAGE IN A MIS DIODE

[75] Inventor: Stephen C. Pyke, 64630 Sylvan Loop, Bend, Oreg. 97701

[73] Assignee: Stephen C. Pyke, Bend, Oreg.

[21] Appl. No.: 300,151

[22] Filed: Jan. 19, 1989

[51] Int. Cl.$^5$ ............................................. G01N 27/00
[52] U.S. Cl. ................................... 324/71.5; 324/71.1; 204/416
[58] Field of Search ...................... 324/71.1, 71.5, 438, 324/439; 204/416, 418, 419; 357/23

[56] References Cited

U.S. PATENT DOCUMENTS

| | | | |
|---|---|---|---|
| 3,719,564 | 3/1973 | Lilly, Jr. et al. | 204/1 T |
| 4,020,830 | 5/1977 | Johnson et al. | 128/2 E |
| 4,180,771 | 12/1979 | Guckel | 204/418 X |
| 4,218,298 | 8/1980 | Shimada et al. | 204/195 M |
| 4,305,802 | 12/1981 | Koshiishi | 204/195 M |
| 4,354,308 | 10/1982 | Shimada et al. | 29/571 |
| 4,368,480 | 1/1983 | Senturia | 357/25 |
| 4,411,741 | 10/1983 | Janata | 204/1 T |
| 4,456,522 | 6/1984 | Blackburn | 204/419 X |
| 4,486,292 | 12/1984 | Blackburn | 357/23 |
| 4,514,263 | 4/1985 | Janata | 204/1 T |
| 4,534,292 | 12/1984 | Blackburn | 204/416 X |
| 4,534,825 | 8/1985 | Koning et al. | 204/416 X |
| 4,671,852 | 6/1987 | Pyke | 156/652 |
| 4,714,673 | 12/1987 | Kezzler et al. | 204/418 X |

OTHER PUBLICATIONS

G. Bailey, *An Integrating 128 Elements InSb Array: Recent Results*, Proceedings of the Society of Photo-Optical Instrumentation Engineers, vol. 345, Paper No. 23, (1982).

"Physics of Semiconductor Devices", Sze, pp. 362-377, 1981.

Primary Examiner—William M. Shoop, Jr.
Assistant Examiner—A. Jonathan Wysocki
Attorney, Agent, or Firm—Howard S. Robbins

[57] ABSTRACT

A metal-insulator-semiconductor (MIS) diode having a suspended electrode forming a cavity between the electrode and the insulator is operated in the charge storage, i.e. inversion, mode to detect a fluid concentration. A reverse bias voltage is applied to the diode to form a charge inversion layer in the semiconductor, the bias is disconnected and subsequently reapplied. The charge that flows upon reapplication of the bias voltage is a measure of the concentration of a fluid in the cavity. An array of MIS diodes with multiplexed biasing and charge measurement permits detection of combinations of different fluids, even in the presence of potentially interfering chemical species.

15 Claims, 1 Drawing Sheet

DEVICE AND METHOD FOR DETECTION OF FLUID CONCENTRATION UTILIZING CHARGE STORAGE IN A MIS DIODE

TECHNICAL FIELD

The present invention relates generally to a device and method for detection of specific components in liquid or gaseous fluids. More particularly, the device and method taught herein utilize the charge storage properties of a metal insulator semiconductor diode to detect characteristics of fluids such as the partial pressure of hydrogen gas.

BACKGROUND ART

Chemically sensitive field-effect transistors (CHEMFETs) have been developed for the detection of specific compounds in liquid and gaseous environments, such as the ion sensitive CHEMFETs disclosed in U.S. Pat. No. 4,020,830 to Johnson, et al. and U.S. Pat. No. 4,305,802 to Koshiishi.

Other CHEMFETs have been produced that measure the concentrations of components in a gaseous state, as for example the devices disclosed in U.S. Pat. No. 3,719,564 to Lilly, Jr., et al. and described by Shimada, et al. in U.S. Pat. Nos. 4,218,298 and 4,354,308, and the suspended gate field-effect transistors (SGFETs) described by Jiri Janata in U.S. Pat. Nos. 4,411,741 and 4,514,263. However, such devices do not provide linear response to the desired components resulting in lower measurement accuracy. These devices are also relatively complex and costly to manufacture due to their multiple junctions and diffusion regions.

CHEMFETs in general, and SGFETs in particular are also not well suited to the detection of combinations of specific compounds or of specific compounds in the presence of other potentially interfering chemical species. Combinations of discrete SGFETs with sensitivities to different compounds have been proposed in efforts to address such deficiencies. For example, in U.S. Pat. No. 4,368,480 to Senturia multiplexed CHEMFETs provide logic elements with varying on-off duty cycles. Nevertheless, such combinations are even more difficult and costly to manufacture than individual sensors.

CHEMFETs, such as those exemplified by U.S. Pat. No. 4,411,741 to Janata and U.S. Pat. No. 4,486,292 to Blackburn, are two-port (i.e., three terminal) devices that monitor environmental fluid concentration by measuring current flow within the semiconductor between the source and drain, i.e., drain current. The background of the Blackburn patent states in-part that the term CHEMFET embraces diode-type devices which feature conductivity modulation similar to that of CHEMFETs.

However, diodes are one-port (i.e., two terminal) devices and therefor have no drain or drain current to measure. Thus, if a MIS diode is to be used to monitor fluid concentration, another device parameter must be employed.

Those ordinarily skilled in the sensor art would measure an MIS diode's capacitance to monitor environmental fluid concentration since capacitance is proportional to surface potential which is in turn proportional to fluid concentration. But the known surface physics of an MIS diode makes clear that such a measurement would not be successful.

The relevant surface physics of MIS diodes may be best appreciated from the renowned text entitled Physics of Semiconductor Devices, (Second Edition—1981) by S. M. Sze. Chapter 7 of that text presents in Sections 7.1 and 7.2 (at pages 362–379, a copy of which accompanies this Amendment) a thorough discussion of MIS diode construction and operation.

The response of MIS diode capacitance to changes in surface potential can be understood by first referring to FIG. 5 (on page 369) which illustrates the variation of space-charge density ($Q_s$) in the semiconductor as a function of the surface potential ($\psi_s$) for an exemplary p-type silicon. As seen in that Figure, changes in space-charge density may be broadly classified as occurring in three modes: accumulation, depletion and weak inversion, and strong inversion.

Only in the depletion and weak inversion mode do changes in surface potential (which are proportional to changes in fluid concentration) produce changes in depletion region depth, which in turn alters space-charge capacitance. However, in this mode the magnitude of changes in depletion region depth vary as the square root of changes in surface potential. Moreover, the skilled artisan will appreciate that capacitance varies in a complex manner with temperature. In other words, operating a MIS diode in this mode would result in a poor, temperature variant fluid concentration sensor.

In the strong inversion mode the skilled artisan would recognize that capacitance cannot be used to monitor fluid concentration because, as depicted in FIG. 9 on page 374, for surface potentials this great the depletion region reaches a fixed minimum depth ($W_m$). Since capacitance is proportional to the depth of the depletion region within the diode semiconductor which under these conditions does not change, diode capacitance could not reflect fluid concentration changes.

DISCLOSURE OF INVENTION

I have discovered that it is possible to accurately monitor fluid concentration, not by measurement of MIS diode capacitance, but by an indirect measurement of space-charge density ($Q_s$) in the strong inversion mode where space-charge density is an exponential function of surface potential. This measurement is accomplished by measuring MIS diode recombination current. Moreover, because of the relationship between space-charge density and chemical effect on surface potential, measuring the recombination current yields a linear, temperature independent monitor of fluid concentration, something not possible based on prior art devices.

Therefore, it is an object of the present invention to provide a semiconductor sensor and an embodied method for furnishing a substantially linear response to selected fluid concentrations.

It is a further object of the present invention to provide a semiconductor sensor, as set forth above, that is less costly to manufacture than suspended gate field-effect transistor sensors.

There and other objects and advantages of the present invention over existing prior art forms will become more apparent and fully understood from the following description in conjunction with the accompanying drawings.

In general, a device in accordance with the present invention for monitoring the concentration of at least one selected fluid includes a metal insulator semiconductor diode sensor having a surface potential proportional to the selected fluid concentration and a carrier recombination rate proportional to the surface potential. Circuitry is provided for selectively biasing the diode to form a charge inversion region and allowing the stored charge in the diode sensor to decay while the diode sensor is in the presence of the selected fluid, and for determining the magnitude of the diode recombination current after the decay. The selected fluid concentration may be calculated from the amount of charge lost in the decay. A plurality of metal insulator semiconductor diodes, at least one of whose surface potential is proportional to the selected fluid concentration and whose carrier recombination rate is proportional to the surface potential, may be connected to a multiplexer for selectively biasing each diode junction into deep inversion and determining each diode's recombination current.

A method for monitoring the concentration of at least one selected fluid includes the steps of biasing the junction of a metal insulator semiconductor diode, whose surface potential is proportional to the selected fluid concentration and whose carrier recombination rate is proportional to the surface potential to form a charge inversion region, removing the voltage bias from the diode, allowing the stored charge in the diode to decay while the diode is in the presence of the selected fluid, determining the amount of charge lost during the decay, and calculating the concentration of the selected fluid from the magnitude of the lost charge. The method may further include the steps of selectively similarly biasing the junctions of a plurality of metal insulator semiconductor diodes, at least one of whose surface potential is proportional to the selected fluid concentration and whose carrier recombination rate is proportional to the surface potential, and determining the charge lost by each diode during a respective decay.

PREFERRED EMBODIMENT FOR CARRYING OUT THE INVENTION

Figure 1:
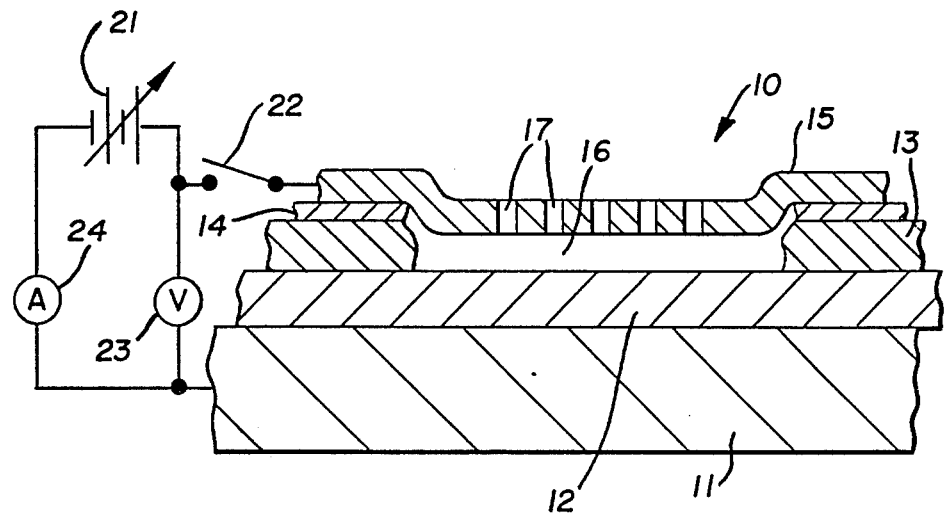
FIG. 1 is an elevational view through an exemplary metal insulator semiconductor diode embodying the concepts of the present invention.

FIG. 1 illustrates a device generally indicated by the numeral 10 for monitoring the concentration of at least one selected liquid or gaseous fluid. Device 10 is referred to as a metal insulator semiconductor (MIS) diode.

MIS diode 10 may be formed of a silicon substrate 11 having p-type doping characteristics, a layer of insulator 12 such as silicon dioxide and/or silicon nitride covering substrate 11 and three metallic layers 13, 14 and 15 applied to the side of insulator 12 opposite substrate 11. Layers 13, 14 and 15 may be made respectively of a fugitive material such as aluminum, and, where MIS diode 10 is to detect the partial pressure of hydrogen, a thin film of tungsten/titanium and a layer of a noble metal such as platinum. The fugitive layer 13 is removed by chemical etching to form a cavity 16 between insulator 12 and metallic layer 15. A selected fluid may flow into cavity 16 through a plurality of holes 17 in suspended electrode 15.

Other than as provided below, the composition and construction of MIS diode 10 is substantially identical to the composition and construction of the suspended gate electrode and substrate portion of the SGFET described in detail in my U.S. Pat. No. 4,671,852 entitled "Method Of Forming Suspended Gate, Chemically Sensitive Field-Effect Transistor", which is hereby incorporated herein by reference. As taught therein, the layers applied atop substrate 11 may be selected such that MIS diode 10 has a surface potential proportional to the concentration of hydrogen, hydrogen sulfide, methane, carbon monoxide, oxygen, alcohols, water vapor or low molecular weight hydrocarbons.

One terminal of a voltage source 21 is electrically connected through a switch 22 to suspended electrode or gate 15. The opposite terminal of voltage source 21 is electrically connected to substrate 11. As explained more fully hereinafter, voltage and/or current measuring devices such as voltmeter 23 and ammeter 24, may be electrically connected to measure the potential across and current flowing between the gate and substrate of MIS diode 10. When a MIS diode is reverse biased with a sufficiently large voltage, less than its breakdown voltage, it is in the so-called charge storage mode. In that mode, the electric field within the p-type substrate adjacent insulator 12 is so strong that a large number of negative charge carriers (electrons) accumulate there. That region actually becomes n-type under the influence of the strong reverse bias voltage and thus is termed an inversion region. Thereby a current flows that is directly dependent on the rate of electron-hole (i.e., charge carrier) recombination. That recombination current is directly controlled by the surface potential at the interface of insulator 12 and semiconductor 11. In turn that surface potential is determined by the surface potential at the surface of insulator 12 that is exposed to cavity 16. In other words, where a suspended gate MIS diode is sufficiently reverse-biased, its carrier recombination rate dictates its leakage current, which in turn is proportional to the MIS diode's surface potential at the suspended electrode.

Since the surface potential at the suspended electrode of a suspended gate MIS diode is proportional to the selected fluid concentration, I have found that measurement of recombination current can be utilized to directly yield fluid concentration. More particularly, I have discovered that independent of temperature the change in the rate of recombination can be made to vary substantially linearly with a change in partial pressure of the fluid of interest. This linear variation can be achieved by careful selection of the suspended electrode 15 metal, the total number of surface sites for that fluid and the adsorption enthalpy. Where, solely by way of example, the partial pressure of hydrogen gas is of interest, use of a platinum suspended electrode 15 having about $10^{17}/cm^2$ surface sites and an adsorption anthalpy in the range of about 10 to about 20 Kcal/mol, yields the desired substantially linear relationship.

Use of MIS diode 10 to determine the partial pressure of hydrogen gas is straightforward. Switch 22 is closed and voltage source 21 applies a sufficiently large reverse potential across MIS diode 10 to bias it into inversion, where it operates MIS diode 10 in the charge storage mode. Switch 22 is then opened and the hydrogen gas allowed to flow through holes 17 into cavity 16.

After a period of time sufficient to allow some decay in the charge stored in the inversion layer in semiconductor 11, switch 22 is again closed. Voltage source 21 again biases MIS diode 10 to the original inversion voltage. Either the current flow or the quantity of electrical charge that flows in the rebiasing may be ascertained from ammeter 24 thereby furnishing a measurement of the recombination current that flowed in the decay. That is, in the restoration of the initial, deep inversion biasing voltage, some current flows from voltage source 21. That current restores the charge carriers that were lost during the decay, when voltage source 21 was disconnected. Thus the charge (i.e. current integrated over time) that flows on rebiasing equals the charge lost in the immediately preceding decay. The absolute partial pressure of hydrogen gas may then be calculated by linear interpolation from the magnitude of current flow or charge measured under similar circumstances, but with a known partial pressure. Of course, where only the relative change in partial pressure is of interest, the current that flows upon the successive closings of switch 22 will directly yield that change.

Where greater noise immunity, redundancy, or ability to detect combination of specific compounds or specific compounds in the presence of other potentially interfering chemical species is desired, it is preferable to form a plurality of MIS diodes in an array, together with a suitable multiplexer (MUX) to selectively bias, allow to discharge, rebias and measure recombination current on each MIS diode in the array.

Figure 2:
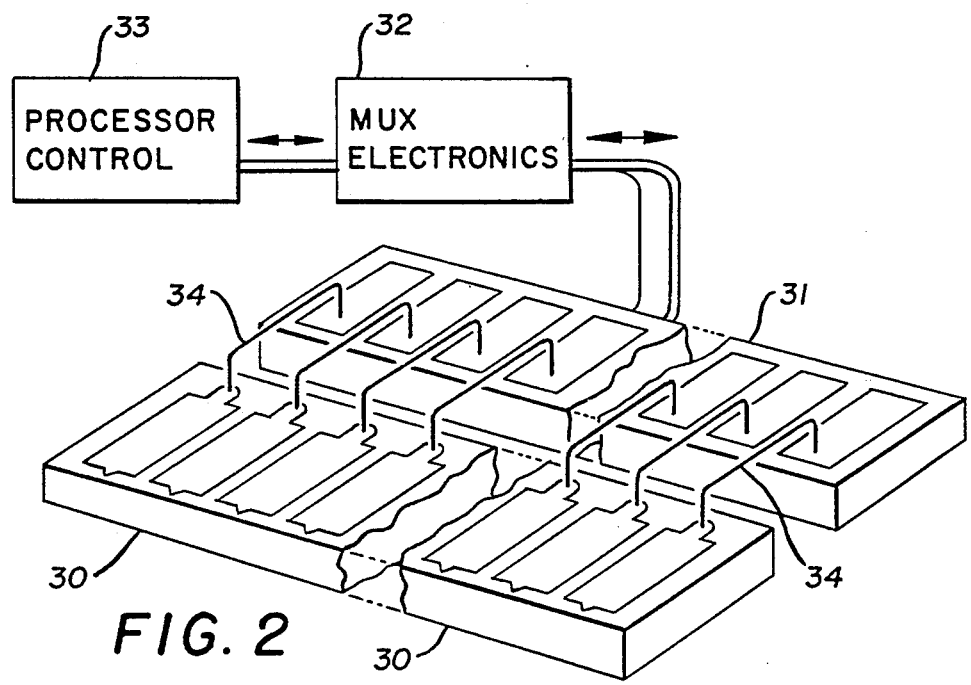
FIG. 2 is a perspective view of a portion of an array of metal insulator semiconductor diodes embodying the concepts of the present invention and a corresponding portion of a multiplexer, and further depicts the multiplexer electronics and processor control circuitry in block diagram form.

FIG. 2 depicts a portion of an array of MIS diodes 30 which may be integrally formed with a silicon MUX 31, MUX electronics 32 and processor control 33, such as is identified and disclosed in detail in the publication by Gary Bailey entitled "An integrating 128 element InSb array: recent results", Proceedings of the Society of Photooptical Instrumentation Engineers, Vol. 345, Paper No. 23, 1982, incorporated herein by references.

Each MIS diode which forms a part of array 30 is electronically connected to its corresponding MUX 31 element by respective wire conductors 34. Each MIS diode may be provided with suspended electrode materials suitable for sensitivity to a desired fluid and in this manner a multiple gas and fail-safe detector may be achieved.

Those skilled in the art will appreciate that as discussed in the Bailey publication, supra, since the array of MIS diodes 30 are being operated in the charge storage mode, it is highly desirable to minimize MIS diode capacitance. That capacitance should dominate the combined series capacitance of the MIS diode and the MUX, to isolate each suspended electrode from capacitive cross-talk with neighboring MIS diodes in the array.

It has been found that in the exemplary hydrogen sensor noted above, an array of 64 substantially identical MIS diodes formed in the same package including a 64 element MUX having center to center element spacing of 125 micrometers, that acceptable operation was obtained. The insulator had a combined thickness of 1000 Angstroms and was formed of silicon dioxide and silicon nitride on <100> oriented crystalline silicon doped at $10^{15}/cm^3$. The sensors in the array included suspended electrode pads 100 micrometers wide by 2000 micrometers long and covered with 5 micrometer diameter holes spaced 20 micrometers between centers. Isolation between adjacent sensors may be achieved by any of the mechanisms well known in the art, such as diffusing an n-type doping characteristic guarding into the substrate around each MIS diode.

Inasmuch as the present invention is subject to variations, modifications and changes in detail, a number of which have been expressly stated herein, it is intended that all matter described throughout this entire specification or shown in the accompanying drawings be interpreted as illustrative and not in a limiting sense. It should thus be evident that a device constructed according to the concept of the present invention, and reasonably equivalent thereto, will accomplish the objects of the present invention and otherwise substantially improve the art of monitoring the concentration of selected liquid or gaseous fluids.

I claim:

1. Apparatus for monitoring the concentration of at least one fluid comprising:

a metal-insulator-semiconductor diode including a semiconductor substrate, an electrical insulator disposed on said substrate, and a metal electrode overlying said insulator, at least a portion of said electrode being spaced from said insulator to form a cavity therebetween, said semiconductor having a surface potential proportional to the concentration of a fluid disposed in said cavity;

voltage source means electrically connected to said semiconductor and said electrode for applying a reverse bias voltage to the diode to form a charge inversion region in the semiconductor adjacent said insulator and for, from time to time, removing and thereafter reapplying said reverse bias voltage; and electrical charge measuring means for measuring the quantity of electrical charge that flows from said voltage source means when said reverse bias voltage is reapplied to said diode after being removed from said diode.

2. The apparatus of claim 1 wherein said electrode is platinum.

3. The apparatus of claim 1 wherein said semiconductor is p-type silicon.

4. The apparatus of claim 1 wherein said insulator is at least one of silicon dioxide and silicon nitride.

5. The apparatus of claim 1 wherein said electrode includes holes for admitting a fluid into and draining a fluid from said cavity.

6. Apparatus for monitoring the concentration of at least one fluid comprising:

a plurality of metal-insulator-semiconductor diodes, each diode including a semiconductor substrate, an electrical insulator disposed on said substrate, and a metal electrode overlying said insulator, at least a portion of said electrode being spaced from said insulator to form a cavity therebetween, said semiconductor having a surface potential proportional to the concentration of a fluid disposed in said cavity;

multiplexed voltage source means electrically connected to said semiconductor and said electrode of each of said diodes for applying to each of said diodes a reverse bias voltage to form in each diode a charge inversion region in the semiconductor adjacent said insulator and for, from time to time, removing and thereafter reapplying to each of said diodes said reverse bias voltage; and multiplexed electrical charge measuring means for measuring the quantity of electrical charge that flows from said multiplexed voltage source means into each diode when said reverse bias voltage is reapplied to a said respective diode after being removed from said respective diode.

7. The apparatus of claim 6 wherein at least one of said electrodes is platinum.

8. The apparatus of claim 6 wherein said diodes all have a common substrate of p-type silicon.

9. The apparatus of claim 6 wherein said insulator is at least one of said diodes is at least one of silicon dioxide and silicon nitride.

10. The apparatus of claim 6 wherein at least one of said electrodes includes holes for admitting a fluid into and draining a fluid from the cavity formed between said electrode and said insulator.

11. A method of monitoring the concentration of a fluid comprising:

applying a reverse bias voltage to a metal-insulator-semiconductor diode including a semiconductor substrate, an electrical insulator disposed on said substrate, and a metal electrode overlying said insulator, at least a portion of said electrode being spaced from said insulator to form a cavity therebetween, said semiconductor having a surface potential proportional to the concentration of a fluid disposed in said cavity, to form a charge inversion region in the semiconductor adjacent said insulator;

removing said voltage bias from said diode and subsequently reapplying said reverse bias voltage;

measuring the quantity of the electrical charge that flows into said diode when said reverse bias voltage is reapplied; and calculating the concentration of the selected fluid in said cavity from said quantity of charge.

12. The method of claim 11 including measuring the quantity of electrical charge by measuring the current as a function of time that flows to said diode when the reverse bias voltage is reapplied.

13. A method of monitoring the concentration of a fluid comprising applying a reverse bias voltage to each of a plurality of metal-insulator-semiconductor diodes, each diode including a semiconductor substrate, an electrical insulator disposed on said substrate, and a metal electrode overlying said insulator, at least a portion of said electrode being spaced from said insulator to form a cavity therebetween, said semiconductor having a surface potential proportional to the concentration of a fluid disposed in said cavity, to form a charge inversion region in the semiconductor adjacent to said insulator in each of said diodes;

removing from said bias voltage from at least one of said diodes and subsequently reapplying said reverse bias voltage to said at least one diode;

measuring the quantity of electrical charge that flows to said at least one diode when said bias voltage is reapplied; and calculating the concentration of the selected fluid in said cavity from said quantity of charge.

14. The method of claim 13 including measuring the quantity of electrical charge by measuring the current as a function of time that flows to said at least one diode when the reverse bias voltage is reapplied.

15. The method of claim 13 wherein said step of removing said bias voltage includes sequentially removing said voltage from each said diode.

* * * * *

UNITED STATES PATENT AND TRADEMARK OFFICE
CERTIFICATE OF CORRECTION

PATENT NO. : 4,947,104
DATED : August 7, 1990
INVENTOR(S) : Stephen C. Pyke It is certified that error appears in the above-identified patent and that said Letters Patent is hereby corrected as shown below:

On the title page: Item [56]

References Cited, U.S. Patent No. 4,534,292 should be deleted.

Column 1, line 67, "an" should read --a--.

Column 2, lines 2-3, "Physics of Semiconductor Devices" should be in italics.

Column 2, lines 5-6, ", a copy of which accompanies this Amendment" should be deleted.

Column 2, line 23, "square root" should be in italics.

Column 2, line 61, "There" should read --These--.

Column 3, line 24, "potential" should read --potential,--.

Column 4, line 24, "When a MIS diode..." should begin a new paragraph.

Column 5, line 19, "partial pressure", should read --hydrogen partial pressure--.

UNITED STATES PATENT AND TRADEMARK OFFICE
CERTIFICATE OF CORRECTION

PATENT NO. : 4,947,104

DATED : August 7, 1990

INVENTOR(S) : Stephen C. Pyke

It is certified that error appears in the above-identified patent and that said Letters Patent is hereby corrected as shown below:

Column 5, line 30, "on each" should read --of each--.

Column 5, line 38, "references" should read --reference--.

Column 6, line 1, "guarding" should read --guard-ring--.

Signed and Sealed this

Third Day of August, 1993

Attest:

MICHAEL K. KIRK

*Attesting Officer*     *Acting Commissioner of Patents and Trademarks*